United States Patent
Blomqvist et al.

(10) Patent No.: US 8,355,782 B2
(45) Date of Patent: Jan. 15, 2013

(54) IMPLANTABLE HEART STIMULATOR FOR MEASURING DYSSYNCHRONY USING IMPEDANCE

(75) Inventors: Andreas Blomqvist, Spånga (SE); Nils Holmström, Järfälla (SE); Malin Öhlander, Stockholm (SE); Sven-Erik Hedberg, Kungsängen (SE)

(73) Assignee: St. Jude Medical AB, Jarfalla (SE)

( * ) Notice: Subject to any disclaimer, the term of this patent is extended or adjusted under 35 U.S.C. 154(b) by 77 days.

(21) Appl. No.: 12/863,381

(22) PCT Filed: Jan. 28, 2008

(86) PCT No.: PCT/SE2008/000077
§ 371 (c)(1),
(2), (4) Date: Jul. 16, 2010

(87) PCT Pub. No.: WO2009/096819
PCT Pub. Date: Aug. 6, 2009

(65) Prior Publication Data
US 2010/0298904 A1    Nov. 25, 2010

(51) Int. Cl.
*A61N 1/365*    (2006.01)
(52) U.S. Cl. .................. 607/17; 607/9; 607/18; 607/28
(58) Field of Classification Search ............... 607/11, 607/17
See application file for complete search history.

(56) References Cited

U.S. PATENT DOCUMENTS

| | | | |
|---|---|---|---|
| 7,082,329 B2 | 7/2006 | Järverud | |
| 7,805,194 B1* | 9/2010 | Schecter | 607/17 |
| 2004/0078058 A1* | 4/2004 | Holmstrom et al. | 607/17 |
| 2006/0271117 A1 | 11/2006 | Burnes et al. | |
| 2007/0005114 A1 | 1/2007 | Salo et al. | |
| 2007/0043394 A1 | 2/2007 | Zhang et al. | |
| 2007/0066905 A1 | 3/2007 | Zhang | |
| 2007/0078356 A1* | 4/2007 | Faber et al. | 600/518 |
| 2007/0142866 A1* | 6/2007 | Li et al. | 607/17 |
| 2007/0179390 A1 | 8/2007 | Schecter | |
| 2008/0262361 A1 | 10/2008 | Gutfinger et al. | |

FOREIGN PATENT DOCUMENTS

WO    WO 2009/082284    7/2009

OTHER PUBLICATIONS

"Dicrotic Notch Detection Using Wavelet Transform Analysis," Antonelli et al., IEEE 1994 pp. 1216-1217.
An Innovative Dicrotic notch Detection Algorithm Which Combines Rule-Based Logic with Digital Signal Processing Techniques, Oppenheim et al., Computers and Biomedical Research, vol. 28 (1995) pp. 154-170.

* cited by examiner

*Primary Examiner* — Niketa Patel
*Assistant Examiner* — Minh Duc Pham

(57) ABSTRACT

Implantable heart stimulator connectable to an electrode arrangement has a pulse generator adapted to deliver stimulation pulses to a heart of a subject; an impedance measurement unit adapted monitor at least one heart chamber of the heart of the subject to measure the impedance in the at least one monitored heart chamber for generating an impedance signal corresponding to the measured impedance. The impedance signal is applied to a processor where the signal is processed, according to specified criteria, and a fractionation index value is determined represented by the curve length of the impedance signal during a predetermined measurement period. The fractionation index value is a measure of different degrees of mechanical dyssynchrony of the heart.

8 Claims, 2 Drawing Sheets

IMPLANTABLE HEART STIMULATOR FOR MEASURING DYSSYNCHRONY USING IMPEDANCE

BACKGROUND OF THE INVENTION

1. Field of the Invention

The present invention relates to an implantable heart stimulator, and a method for detecting a state of mechanical dyssynchrony of the heart of a patient, according to the preambles of the independent claims.

2. Description of the Prior Art

Many patients with advanced systolic heart failure exhibit significant intra- or interventricular conduction delays (IVCD) that disturb the synchronous beating of the ventricles so that they pump less efficiently. This delayed ventricular activation and contraction is referred to as ventricular dyssynchrony and is often seen as a wide QRS complex with a left bundle branch block morphology on ECG.

Ventricular dyssynchrony has been shown to have a number of deleterious effects on cardiac function, including reduced diastolic filling time, weakened contractility, protracted mitral regurgitation, and post-systolic regional contraction that together result in diminished stroke volume.

Cardiac resynchronization therapy (CRT), which is sometimes called biventricular pacing, is a new form of therapy for congestive heart failure caused by dilated cardiomyopathy. Several studies now document the remarkable benefits conferred by CRT on appropriately selected patients with heart failure.

CRT uses a specialized pacemaker to re-coordinate the contraction of the right and left ventricles in patients with heart failure.

In approximately 30% of patients with heart failure, an abnormality in the heart's electrical conducting system causes the two ventricles to beat in an asynchronous fashion. That is, instead of beating more or less simultaneously, the two ventricles beat slightly out of phase. This asynchrony greatly reduces the efficiency of the ventricles in patients with heart failure, whose hearts are already damaged.

CRT re-coordinates the beating of the two ventricles by pacing both ventricles simultaneously. This differs from typical pacemakers, which pace only the right ventricle.

Early studies with CRT demonstrated its ability to improve the symptoms, the exercise capacity, and the feeling of well-being of many patients with moderate to severe heart failure. Additional studies showed that CRT can improve both the anatomy and function of the heart—tending to reduce the size of the dilated left ventricle, and improving the energy usage of the heart.

Left ventricular dyssynchrony can lead to adverse cardiac effects, particularly if left untreated. As discussed above dyssynchrony can be improved by cardiac resynchronization therapy, but accurate diagnosis of the disorder is essential to obtain good results.

U.S. Pat. No. 7,082,329 relates to a method and monitor for monitoring diastolic relaxation of a heart ventricle by measuring an impedance signal in a ventricle of the heart and detecting the occurrence of a notch in the impedance signal coincident with the entry of blood into the monitored ventricle. The impedance signal is processed by studying the time derivative of the impedance signal which thus enables early detection of congestive heart failure.

In investigations it has been shown that cardiac mechanical dyssynchrony is visible in the morphology of the cardiogenic impedance (CI) signal. In addition it has been shown to study the fractionation of the CI-signal.

Fractionation means, in this context, that the curve length, e.g. being one or several additional notches in the CI-signal that may be identified if the signal is fractionated, or divided, in its parts. These notches, resulting in an increased curve length, are not present during synchronized contractions.

However, there exist no efficient way of automating the procedure of determining the fractionation, and in particular a procedure that requires a low level of processing capacity which is a presumption for use in an implantable heart stimulator having strict power consumption requirements.

SUMMARY OF THE INVENTION

In a method and implantable heart stimulator in accordance with the present invention, a pulse generator delivers stimulation pulses to the heart of a patient, and an impedance measurement unit monitors at least one heart chamber of the heart by measuring impedance thereof in order to generate an impedance signal. The impedance signal is supplied to a computerized processor, wherein a fractionation index value is determined that is represented by the curve length of the impedance signal during a predetermined measurement period. The fractionation index value is used as a measure of different degrees of mechanical dyssynchrony of the heart.

In particular the invention relates to a simple implementation that does not require any advanced processing and which easily may be implemented in an implantable heart stimulator.

The basis of the present invention, and identified by the inventors, is that an increased fractionation of the impedance signal correlates with worsening heart failure.

Preferably, the waveform is normalized with respect to maximum amplitudes as well as with respect to the R-R-interval. Then the length of the resulting waveform is calculated, somewhat like a line integral. This length may then be used as a fractionation index value that increases with increased fractionation.

A significant benefit of the present invention is that it is not necessary to manually neither define, nor detect the notches which totally remove human bias, and there is never going to be any "difficult decisions" since the determined curve length is simply the basis for all analysis.

According to one preferred embodiment the heart stimulator is adapted to trend the heart failure by measuring the fractionation index value at a given time interval. An alert may preferably be generated if a sudden drastic change in the trend occurs.

According to another preferred embodiment the heart simulator is adapted to adjust the timing between generated stimulation pulses such that fractionation index value is minimized, this may be performed e.g. in order to optimize the VV-delay in CRT devices.

Thus, as discussed above it is important that the algorithm used to determine the fractionation index value is comparatively low-computational, i.e. requires a small amount of energy to be processed. This is due to the fact that the implantable medical device has a limited power supply.

DESCRIPTION OF THE PREFERRED EMBODIMENTS

Previously there was only a very tedious way of calculating the fractionation, and indeed only feasible to do by hand. This is of course not suitable for implementing in an implantable medical device. The procedure was to filter the signal properly, then look at all the notches.

Initially, a suitably stable part of the CI-signal, without too much respiration artefacts had to be chosen manually from the recording.

Every notch that was larger than 25% of the maximum amplitude span of each heart cycle was considered a notch. The number of these notches from a certain number of heartbeats was then averaged into the value stored away as the fractionation index.

To implement such a procedure, rather advanced processing may be required, which is not preferred, with regard to the power consumption, but nevertheless naturally would be possible to include into an implantable medical device.

In short the above procedure may be performed by the following steps:
Filter the signal to make it smooth and rather noise free.
Perform another filtering to isolate the respiratory peaks so that a section between these peaks could be chosen.
Then the resulting signal would have to be processed a third time in which all local maxima and minima need to be identified.
After that, each and every one of these min-max pairs has to be compared to the global min-max of each heartbeat, and then finally averaged resulting in the fractionation index value.

As indicated above the present invention may be implemented by use of the above procedure, however, the embodiments disclosed in the following are considered more advantageous.

Figure 1:
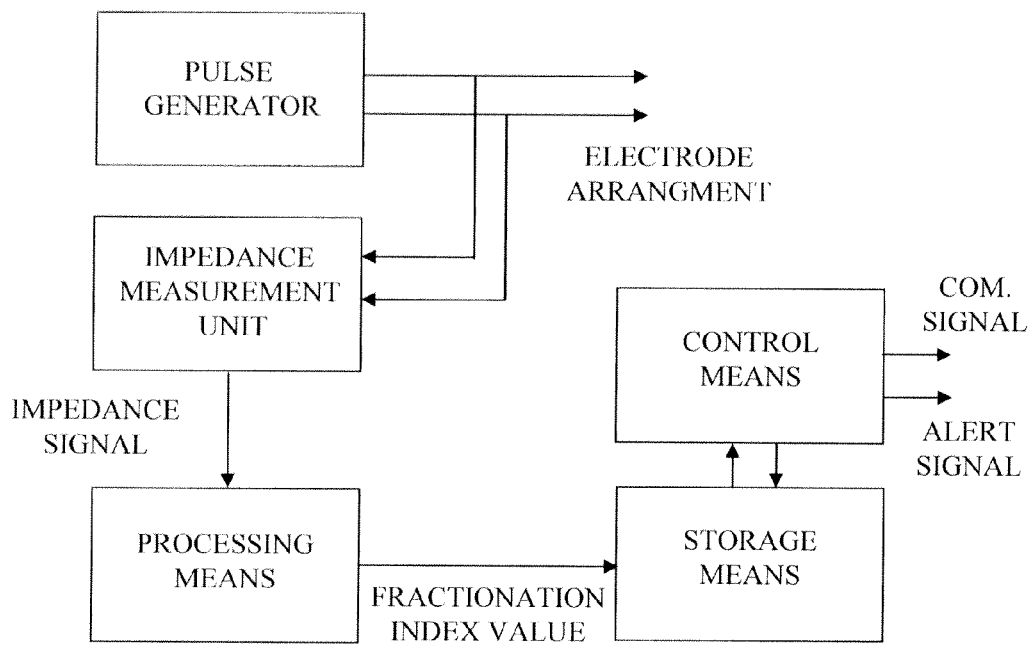
FIG. 1 shows a block diagram schematically illustrating the present invention.

With references to the schematic block diagram shown in FIG. 1, which illustrates an implantable heart stimulator according to the present invention, the invention will now be described in detail.

The implantable heart stimulator comprises a pulse generator connectable to an electrode arrangement adapted to deliver stimulation pulses to a heart of a subject, an impedance measurement unit adapted to monitor at least one heart chamber of the subject by measuring the impedance of the at least one monitored heart chamber for generating a signal corresponding to the impedance.

Many different configurations may be applicable in order to obtain the impedance signal. It might be preferable to use bi- (or uni-) polar measurement configurations as opposed to using quadro- or tri-polar configurations. This is since the polarization effects causes the signal content in the bipolar configurations to reflect the myocardium and its movements to a greater extent, whereas the multi-polar configurations bypass that contact potential, thus containing more information about the blood volumes in the chambers of the heart. It has also been shown that very much of the mechanical activity of the left side is visible by performing local impedance measurements, e.g. a bipolar measurement in the right ventricular apex. However, results consistent with the theory underlying the present invention have been obtained using other configurations as well.

The obtained impedance signal is applied to a processing means where the signal is processed, according to specified criteria, and a fractionation index value is determined represented by the curve length of the impedance signal during a predetermined measurement period, wherein the fractionation index value being a measure of different degrees of mechanical dyssynchrony of the heart. The predetermined measurement period may be determined as the duration of e.g. 10-20 heartbeats, or as a fixed time, e.g. in the range of 10-30 seconds.

The fractionation index value is determined at regular intervals, e.g. once every day, once every second day, once a week, or at any other suitable interval, during a predetermined time period, or during periods specified by the physician, or when specified conditions occur, or constantly, and the resulting fractionation index values are stored in a storage means of the heart stimulator.

The heart stimulator further comprises a control means responsible for the overall control of the heart stimulator, e.g. determines which pacing regimen should be applied, and handles communication to an external device via conventional telemetry.

The stored fractionation index values may be processed by the control means of the implantable stimulator, or may be transferred via conventional telemetry to the external device for further analysis.

According to a preferred embodiment the stored fractionation index values are compared, by the control means, to specified thresholds representing different degrees of heart failure, and an alert signal, e.g. a vibration signal or an audible signal, is generated if a stored fractionation index value exceeds a specified threshold representing a dangerous degree of heart failure.

According to another preferred embodiment of the implantable heart stimulator the timing between stimulation pulses generated by the pulse generator is adjusted, by the control means, such that the determined corresponding fractionation index value is minimized. In particular the timing may relate to the VV-delay in a biventricular heart stimulator, but other time intervals may naturally also be adjusted as a result of the optimization procedure, e.g. the AV-delay.

As fractionation is a sign of ventricular dyssynchrony a preferred use of the present invention is therefore to optimize the VV-delay in CRT devices. The objective of CRT is to re-synchronize the ventricles and as the fractionation index gives a relative measure of how much dyssynchrony is present, it is suggested the implementation of a control loop, where a certain VV-delay is tested, the fractionation is measured, the VV-delay is altered, the fractionation is measured again, and so on. When a suitable number of delays have been tested, the one yielding the lowest fractionation value is chosen as the best one. This check can be performed as often as desired, but perhaps once a week would be suitable.

In order to determine the curve length the processing means is adapted to perform the following procedure in accordance with a first embodiment:
Average >10 s of data into an average waveform (storing the average R-R-interval from the included heartbeats).
Divide this new waveform by its maximum value.
Sum up the absolute difference between adjacent samples.
Divide by the stored average R-R-interval which results in the final output.

More in detail, the first embodiment is performed by the following steps:
a1) filtering the impedance signal to remove noise;
a2) averaging the impedance signal during the measurement period, preferably being larger than 10 seconds;
b1) storing the average waveform;
b2) storing the average R-R interval from the included heartbeats;
b3) divide the stored average waveform by its maximum value;

b4) summing up the absolute difference values between adjacent samples in the divided stored average waveform, wherein the sum being a measure of the curve length during the measurement period, and c1) dividing the resulting sum of sub-step b4) by the stored average R-R interval and the result being the fractionation index value.

In order to determine the curve length the processing means is adapted to perform the following procedure in accordance with a second embodiment:

For a given number of heartbeats, calculate the sum up to the absolute difference between samples for each heartbeat and then normalize by the number of heartbeats. To remove the influence of noise in the signal, instead of calculating the absolute difference between samples next to each other, calculate the difference between samples further apart (e.g. below 8) and normalize by that separation.

More in detail, the second embodiment is performed by the following steps:

b'1) calculating, for each heartbeat in the measurement period, the absolute difference between samples separated a preset number of samples, e.g. 8;

b'2) summing up the calculated differences in b'1) for each heartbeat;

b'3) normalizing the sum calculated in b'2);

c'1) summing up the normalized sums determined in sub-step b'3) for all heartbeats during a measurement period, and c'2) dividing the sum determined in sub-step c'1 by the number of heartbeats during a measurement period and the result of the division being the fractionation index value.

The fractionation index value, the FI-value, is thus determined, according to the above second embodiment, by the following equation:

$$FI\text{-value} = \frac{1}{R}\sum_{r=1}^{R}\left(\frac{1}{p2p_r \cdot RRint_r \cdot 8}\sum_{n=1}^{N}|(Zc(n+8)-Zc(n))|\right)$$

In the equation R is the number of heartbeats during a measurement period, $p2p_r$ is the peak-to-peak value of beat number r, N is the number of samples during one heartbeat, $RRint_r$ is the RR-interval for heartbeat number r and Z(n) is the impedance value in sample n.

The present invention also relates to a method in an implantable heart stimulator comprising a pulse generator adapted to deliver stimulation pulses to a heart of a subject, and an impedance measurement unit including an electrode arrangement adapted to interact with at least one monitored heart chamber of the heart of the subject to measure an impedance, in the at least one monitored heart chamber, for generating an impedance signal corresponding to the impedance.

Figure 2:
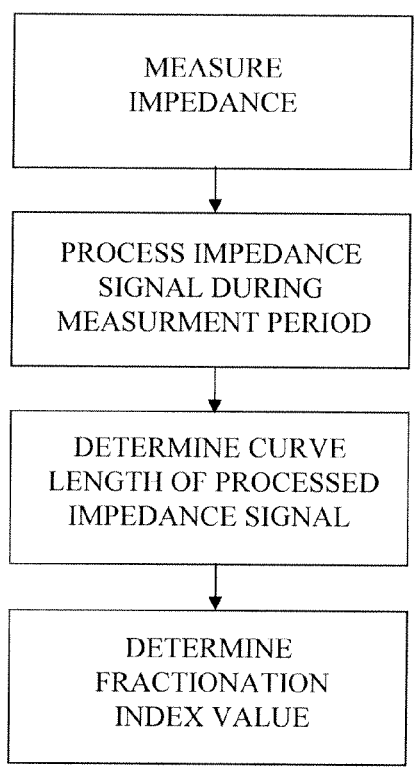
FIG. 2 shows a flow diagram illustrating the present invention.

A flow diagram illustrating the method is shown in FIG. 2.

The method includes the steps of:

a) processing the impedance signal during a measurement period according to specified criteria;

b) determining the curve length of the processed impedance signal during the measurement period;

c) determining a fractionation index value represented by the determined curve length, wherein the fractionation index value being a measure of different degrees of mechanical dyssynchrony of the heart.

The fractionation index value is determined at regular intervals during a predetermined time period (see above) and the resulting fractionation index values are stored in a storage means of the heart stimulator.

According to a preferred embodiment the stored fractionation index values are compared to specified thresholds representing different degrees of heart failure, and an alert signal is generated if a stored fractionation index value exceeds a specified threshold representing a dangerous degree of heart failure.

According to another preferred embodiment the timing between stimulation pulses generated by said pulse generator is adjusted such that the determined corresponding fractionation index is minimized.

The curve length of the impedance signal is preferably determined by the method in accordance with one of the procedures outlined above.

Figure 3:
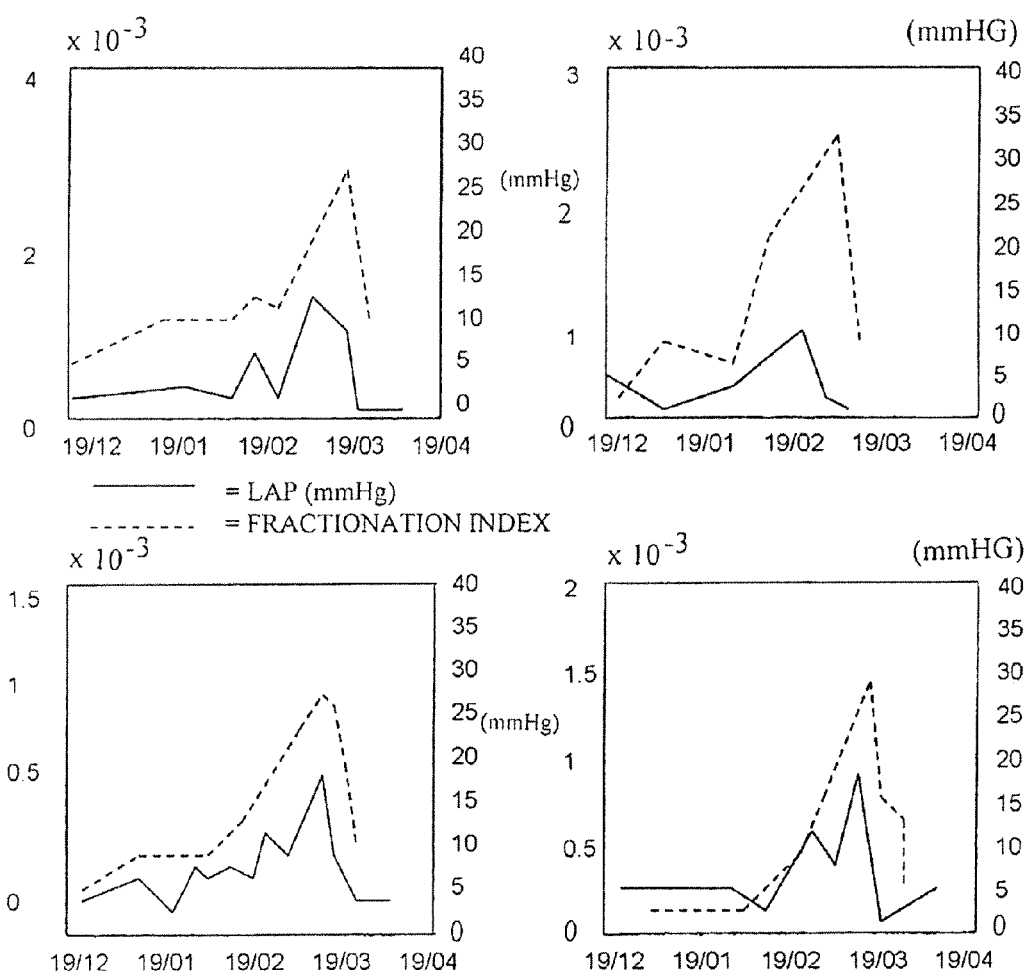
FIG. 3 shows graphs illustrating the present invention.

FIG. 3 shows four diagrams of four different individuals. The diagrams show clearly how the calculated fractionation index (dashed line) trends the heart failure represented by measured left atrial pressure (LAP) (solid line). The x-axis indicates the date when the data was recorded, the right-most axis is the LAP in mm Hg and the left axis shows the value of the fractionation index.

It has been noted that the largest differences in fractionation appear during diastole, and therefore it may be considered advantageous to only include the impedance signal obtained during the diastolic part of the heart cycle in order to increase the specificity of the method.

Although modifications and changes may be suggested by those skilled in the art, it is the intention of the inventors to embody within the patent warranted heron all changes and modifications as reasonably and properly come within the scope of their contribution to the art.

We claim as our invention:

1. An implantable heart stimulator comprising:

an electrode arrangement adapted for placement adjacent a heart of a subject;

a pulse generator adapted for connection to the electrode arrangement to deliver stimulation pulses to the heart;

an impedance measurement unit that monitors, through said electrode arrangement, a chamber of the heart by measuring impedance therein to generate an impedance signal corresponding to said impedance; and a computerized processor supplied with said impedance signal, said computerized processor being configured to analyze said impedance signal according to predetermined criteria to determine a fractionation index value that represents a measure of a length of curve of the impedance signal during a predetermined measurement period of said impedance, said processor making said fractionation index value available at an output thereof as an indicator of a degree of mechanical dyssynchrony of the heart, wherein said processor determines said curve length by filtering the impedance signal to remove noise therefrom, averaging the impedance signal during the measurement period to generate an average waveform, storing the average waveform, storing an average R-R interval from heartbeats included in said impedance signal, dividing the stored average waveform by a maximum value thereof, sampling the stored average waveform to define the number of samples in a heartbeat summing a plurality of absolute difference values between adjacent samples in the stored average waveform that is divided by the maximum to obtain a sum that is a measure of the curve length during the measurement period, and dividing said sum by the stored average R-R interval to obtain a quotient that is said fractionation index value.

2. An implantable heart stimulator as claimed in claim 1 wherein said computerized processor is configured to determine said fractionation index value at regular intervals during a predetermined time period, and to store respective fractionation index values in a memory.

3. An implantable heart stimulator as claimed in claim 2 wherein said processor is configured to access the stored fractionation values and to compare the accessed fractionation index values to respective predetermined thresholds that respectively represent different degrees of heart failure.

4. An implantable heart stimulator as claimed in claim 3 wherein said processor is configured to emit an alert signal when in accessed fractionation index value exceeds one of said predetermined thresholds that represents a dangerous degree of heart failure.

5. An implantable heart stimulator as claimed in claim 1 wherein said processor is configured to adjust a timing between stimulation pulses emitted by said pulse generator to minimize said fractionation index value.

6. An implantable heart stimulator as claimed in claim 5 wherein said pulse generator is a biventricular pulse generator that generates pulses supplied to respective ventricles of the heart with a VV-delay therebetween, and wherein said processor adjusts said timing by adjusting said VV-delay.

7. An implantable heart stimulator as claimed in claim 1 wherein said processor determines said curve length only during a diastolic portion of a heart cycle of the heart.

8. An implantable heart stimulator comprising:
an electrode arrangement adapted for placement adjacent a heart of a subject;
a pulse generator adapted for connection to the electrode arrangement to deliver stimulation pulses to the heart;
an impedance measurement unit that monitors, through said electrode arrangement, a chamber of the heart by measuring impedance therein to generate an impedance signal corresponding to said impedance; and
a computerized processor supplied with said impedance signal, said computerized processor being configured to analyze said impedance signal according to predetermined criteria to determine a fractionation index value that represents a measure of a length of curve of the impedance signal during a predetermined measurement period of said impedance, said processor making said fractionation index value available at an output thereof as an indicator of a degree of mechanical dyssynchrony of the heart, wherein said processor determines said curve length by calculating, for each heartbeat in the measurement period, an absolute difference between measurement samples separated by a predetermined number of samples, summing the calculated differences for each heartbeat to obtain a sum, normalizing the sum, summing each normalized sum for all heartbeats during a measurement period to obtain a sum of normalized sums, and dividing the sum of normalized sums by the number of heartbeats occurring in said measurement period to obtain a quotient that is said fractionation index value.

* * * * *